United States Patent
Furth et al.

(10) Patent No.: US 8,467,499 B2
(45) Date of Patent: Jun. 18, 2013

(54) MULTI-LEAF COLLIMATORS

(75) Inventors: Mark Alexander Furth, Crawley (GB); Adrian Maxwell Smith, London (GB)

(73) Assignee: Elekta AB (Publ), Stockholm (SE)

(*) Notice: Subject to any disclaimer, the term of this patent is extended or adjusted under 35 U.S.C. 154(b) by 219 days.

(21) Appl. No.: 12/988,596

(22) PCT Filed: Apr. 21, 2008

(86) PCT No.: PCT/EP2008/003179
§ 371 (c)(1), (2), (4) Date: Oct. 19, 2010

(87) PCT Pub. No.: WO2009/129816
PCT Pub. Date: Oct. 29, 2009

(65) Prior Publication Data
US 2011/0049396 A1    Mar. 3, 2011

(51) Int. Cl.
*G21K 1/04* (2006.01)

(52) U.S. Cl.
USPC .................................................. 378/152

(58) Field of Classification Search
USPC ................. 378/147, 149–152; 250/505.1
See application file for complete search history.

(56) References Cited

U.S. PATENT DOCUMENTS

| | | | |
|---|---|---|---|
| 4,868,843 A | 9/1989 | Nunan | 378/152 |
| 4,868,844 A * | 9/1989 | Nunan | 378/152 |
| 7,564,951 B2 * | 7/2009 | Hasegawa et al. | 378/152 |
| 2004/0062353 A1 | 4/2004 | Kato et al. | 378/152 |

OTHER PUBLICATIONS

European Patent Office, *Written Opinion*, International Application No. PCT/EP2008/003179, Feb. 2009.

* cited by examiner

*Primary Examiner* — Jurie Yun
(74) *Attorney, Agent, or Firm* — Sunstein Kann Murphy & Timbers LLP

(57) ABSTRACT

A multi-leaf collimator for a radiotherapy apparatus comprises a plurality of elongate leaves mounted in a carriage, the carriage being mounted on a substrate, wherein the leaves are independently moveable relative to the carriage in a longitudinal direction, and the carriage is moveable in that direction relative to the substrate, and a control apparatus is arranged to receive a signal representing leaf positions relative to the substrate and to control the leaf positions relative to the carriage and the carriage positions relative to the substrate so as to achieve those leaf positions relative to the substrate. Most MLCs sense the current positions of the leaves relative to the substrate. The control apparatus can therefore compare the current leaf positions to the signaled leaf positions, and move the leaves and the carriage accordingly. A corresponding method is also disclosed.

9 Claims, 1 Drawing Sheet

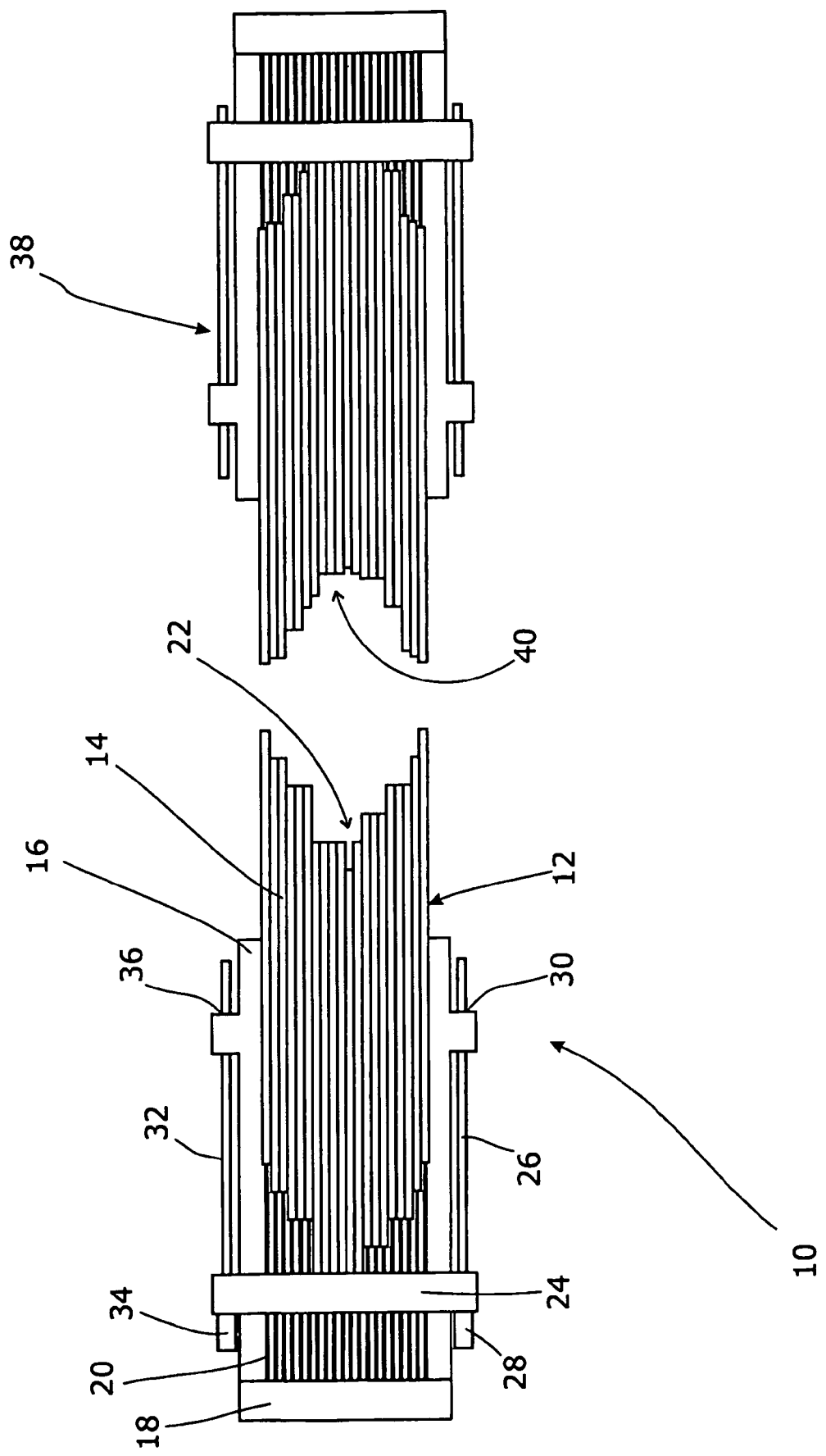

MULTI-LEAF COLLIMATORS

FIELD OF THE INVENTION

The present invention relates to Multi-leaf Collimators.

BACKGROUND ART

A Multi-Leaf Collimator (MLC) is used in external beam radiation therapy in order to collimate the radiation beam to a chosen cross-sectional shape. The aim is to allow accurate delivery of the radiation to the tumour volume, and this is achieved by collimating the beam with an array of narrow elongate tungsten leaves, arranged side-by side and individually motorised in order to allow them to be moved longitudinally. This allows the collimator to define a desired shape.

There are limitations on the longitudinal length of the leaves, dependent on their thickness. Generally, for a given leaf thickness (which does of course define the collimator resolution), there is a maximum feasible length of leaf. Beyond this length, difficulties arise in driving the leaf reliably. This therefore limits the maximum possible collimator aperture, and hence the size of the volume that can be treated. A compromise must therefore be reached between resolution and aperture.

To allow for a greater aperture without compromising resolution, some MLCs mount the leaves on a secondary motion axis, usually referred to as a "carriage". Thus, the leaves are supported on and movable relative to the carriage, and the carriage is mounted on and moveable longitudinally relative to a substrate. This allows collimated shapes to be made in a larger field size than that of a leaf alone. The movements are operated as two distinct axes, operating either on their own or sequentially.

SUMMARY OF THE INVENTION

The present invention therefore provides a multi-leaf collimator for a radiotherapy apparatus, comprising a plurality of elongate leaves mounted in a carriage, the carriage being mounted on a substrate, wherein the leaves are independently moveable relative to the carriage in a longitudinal direction, and the carriage is moveable in that direction relative to the substrate, and a control apparatus arranged to receive a signal representing leaf positions relative to the substrate and being arranged to simultaneously control both the leaf positions relative to the carriage and the carriage positions relative to the substrate, in combination, so as to achieve the signalled leaf positions relative to the substrate.

By allowing the carriage to be driven concurrently with the leaves, the speed of movement of the carriage can be added to that of the leaves. In this way, where leaves are required to make a long traverse they can do so more quickly.

In a carriage-less MLC design, the leaf speeds are limited to that of the single leaf drive provided for each leaf. In a carriage MLC design according to the present invention, the complete leaf motion can be provided by the motion of the individual leaf together with the motion of the carriage that carries the leaves in that bank.

In an conventional MLC incorporating a carriage, the usable leaf speed is still only provided by the individual leaf drives. The carriage position is set independently of the leaf positions and provides a "base point" from which the individual leaves then move. As a result, discontinuities arise during dynamic radiation delivery if the carriage has to be repositioned to allow the leaves to move to new positions not supported by the initial carriage positioning.

Leaf travel and leaf speed are critical parameters in planning and delivering dynamic MLC treatments. Originally, when utilising static treatment shapes, the leaf speed was not critical as it did not alter the machine's ability to deliver the accurate treatment or significantly alter the overall delivery time. With the advent of tumour volume tracking, Volumetric Modulated Arc Therapy (VMAT) and/or Step and Shoot dynamic delivery, the leaves are required to move during delivery of the dose and the maximum usable leaf speed therefore becomes a much more important parameter.

When tracking a tumour volume, the tracking error (i.e. the difference between target shape and the actual delivery shape) is directly related to the difference between required tracking speed and actual available speed. By definition, increasing the available tracking speed or leaf speed will reduce tracking error within faster tracking applications.

When delivering a step and shoot dynamic delivery treatment, the treatment time is directly related to the speed at which the discrete collimating shapes are made because radiation is only delivered when all the leaves are in place.

When delivering a true dynamic or VMAT delivery treatment, the treatment time is directly related to the speed at which the continuous (linearly interpolated) collimating shapes are made. The available speed of all axes (including the leaves) are used to calculate the actual dose rate used within the treatment to ensure a continuous and smooth treatment delivery. Increasing the available leaf speed allows potential selection of a faster dose rate in those instances where leaf motion is the limiting factor.

Previous efforts have therefore been directed to increasing the maximum speed of travel of the leaves, and to extending the maximum length of leaves so that carriage movement during delivery is less likely to be required.

Most MLCs have a means for sensing the current positions of the leaves relative to the substrate, such as an optical or mechanical positional feedback system. The control apparatus can therefore compare the current leaf positions to the signalled leaf positions, and move the leaves and the carriage accordingly. Each leaf can be moved according to a difference between the current leaf position and the signalled leaf position, and the carriage can be moved according to an average difference between the current leaf positions and the signalled leaf positions. The "average" can be a simple calculation such as the arithmetic mean of the respective set of leaf positions, or other arithmetic averages such as the median (or possibly the mode), or it can be a more complex function based on a suitable metric e.g. to maximise delivery speed or minimise tracking error while being bounded by parameters such as maximum speeds, physical limits, design rules etc.

The invention also provides a corresponding method of operating a multi-leaf collimator.

BRIEF DESCRIPTION OF THE DRAWINGS

An embodiment of the present invention will now be described by way of example, with reference to the accompanying FIG. 1, which shows a schematic view of an MLC with a moveable carriage, viewed along the axis of a beam to be collimated by the MLC.

DETAILED DESCRIPTION OF THE EMBODIMENTS

FIG. 1 shows an MLC 10 of the type to which the present application can be applied. A first bank 12 of elongate leaves 10 are arranged in a side-by-side array with their longitudinal edge arranged transverse to the beam, their depth arranged parallel to the beam, and their thicknesses transverse to the beam. Each leaf is mounted in a suitable guide (not shown) supported on a carriage 16. The guide is usually machined so as to support the upper and lower longitudinal edges of the leaves 14 and allow them to slide backwards and forwards in the longitudinal direction. A bank of motors 18, one for each leaf, each drive a leadscrew 20. Each leadscrew 20 engages with a captive nut or other threaded section within a leaf 14; thus as the motor 18 drives the leadscrew 20, this forces the captive nut along the leadscrew 20 and draws the relevant leaf 14 longitudinally backwards or forwards, depending on the direction of rotation of the motor.

In this way, the leaves 14 can be driven so as to define a desired front profile 22 to the collimator.

The carriage itself is mounted on a substrate 24 and is moveable in the same longitudinal direction. It is driven in a similar manner; a carriage screw 26 is driven by a motor 28 on the substrate 24 and engages with a captive threaded portion 30 on one side of the carriage 16. In this example, a duplicate carriage screw 32 is driven by a similar motor 34 and engages with a corresponding captive threaded portion 36 on the opposite side of the carriage 16, to provide a balanced drive.

The entire arrangement is duplicated to form a second leaf bank 38 which is arranged on a diametrically opposite side of the beam. This defines a second collimator front 40. Between the two leaf banks 12, 38, a pair of variable collimator fronts 22, 40 are therefore defined and the beam can be shaped as desired.

To move the leaves of an array to a new position, the motors 18 have hitherto been employed in order to adjust the positions of the leaves 14. However, we have observed that it is often necessary to move all the leaves by a similar amount and/or in the same direction. In this case, the motors 28, 34 can be employed in order to move the carriage 16 (and hence all the leaves 14) in the required direction. This means that if both the leaf motors 18 and the carriage motors 28, 34 are used together, the speed of movement of the leaves can be increased beyond that which the leaf motors 18 are capable of when operating alone.

This invention therefore proposes that the leaf motion be defined as an integrated (single) axis, i.e. that the leaf axis is a composite of both the carriage position and the leaf position rather than being treated as a separate pair of axes. In addition, the leaf position servos are a composite of a leaf position servo and a carriage position servo. This can be referred to as a "dynamic integrated carriage system".

It is proposed the carriages are used to dynamically accommodate the "mean" leaf travel within a leaf bank by using the combined motion and speeds of the carriage and individual leaf drives.

Dynamic Case

In the case of a dynamic or step and shoot treatment, this implies that (according to a defined algorithm) the carriage position is pre-planned so as to minimise treatment time by moving into an optimal position, while (in addition) the individual leaf drives are moving to define the individual positions. This creates the possibility of cumulative leaf speeds greater than that of the individual carriage or leaf drives.

This allows for reduction of treatment time, particularly for sequences of shapes where there is a significant common motion of individual leaves in a leafbank. Such common motion can be assisted by the carriage, through the leaves moving towards their position whilst the carriage is also moving, thus saving time.

A further product of pre-planning the motion of the carriage is that motion discontinuities can be avoided during treatment, because the carriage is actively progressing to the optimal position for the next steps. In effect, the movement of the carriage that would be effected during a discontinuity is commenced in advance so that the carriage is already in position, in time.

A variety of other metrics can be applied to achieving a treatment with the composite leaf and carriage motion described. Examples include leaf travel minimisation, leaf carriage minimisation, delivery time minimisation at the like.

Tracking Case

In the case of a tracking treatment, the treatment is necessarily reactive, so the motion of the carriage or leaves cannot be preplanned. In this case, the composite leaf and carriage servo is used to best track the tumour. The extra available speed is therefore utilised to minimise the tracking error. The reduction of tracking error is a design aim that is assumed will in turn improve the clinical effectiveness of the treatment.

It will of course be understood that many variations may be made to the above-described embodiment without departing from the scope of the present invention.

The invention claimed is:

1. A multi-leaf collimator for a radiotherapy apparatus, comprising:
   a plurality of elongate leaves mounted in a carriage which is mounted on a substrate, wherein the leaves are independently moveable relative to the carriage in a longitudinal direction, and wherein the carriage is moveable in that direction relative to the substrate,
   a control apparatus arranged to receive a signal representing desired leaf positions relative to the substrate and being arranged to simultaneously control both the leaf positions relative to the carriage and the carriage positions relative to the substrate, in combination, so as to achieve the signaled leaf positions relative to the substrate, and
   means for sensing the current positions of the leaves relative to the substrate, wherein the control apparatus moves the carriage according to an average difference between the current leaf positions and the signaled leaf positions.

2. The multi-leaf collimator according to claim 1, wherein the control apparatus compares the current leaf positions to the signaled leaf positions and moves the leaves and the carriage accordingly.

3. The multi-leaf collimator according to claim 1, wherein the control apparatus moves each leaf according to a difference between the current leaf position and the signaled leaf position.

4. The multi-leaf collimator according to claim 1, wherein the average difference considered by the control apparatus is measured by taking the difference between the mean of the current leaf positions and the mean of the signaled leaf positions.

5. A method of operating a multi-leaf collimator:
   the multi-leaf collimator comprising a plurality of elongate leaves mounted in a carriage, the carriage being mounted on a substrate, the leaves being independently moveable relative to the carriage in a longitudinal direction, the carriage being moveable in that direction relative to the substrate, the multi-leaf collimator further comprising means for sensing the current positions of the leaves relative to the substrate;
   the method comprising the steps of receiving a signal representing desired leaf positions relative to the substrate, and simultaneously controlling both the leaf positions relative to the carriage and the carriage positions relative to the substrate, in combination, so as to achieve those leaf positions relative to the substrate, wherein the carriage is moved according to an average difference between the current leaf positions and the signaled leaf positions.

6. The method according to claim 5, wherein the current leaf positions are compared to the signaled leaf positions and the leaves and the carriage are moved accordingly.

7. The method according to claim 5, wherein each leaf is moved according to a difference between the current leaf position and the signaled leaf position.

8. The method according to claim 5, wherein the average difference considered is measured by taking the difference between the mean of the current leaf positions and the mean of the signaled leaf positions.

9. The method according to claim 5, wherein the step of simultaneously controlling includes minimizing one or more of leaf travel, carriage travel and delivery time.

* * * * *